ID009562906B2

United States Patent
Lim et al.

(10) Patent No.: US 9,562,906 B2
(45) Date of Patent: Feb. 7, 2017

(54) METHODS FOR DETECTION OF GASTRIC CANCER

(75) Inventors: Yoon Pin Lim, Singapore (SG); Shirly Poh Kuan Chong, Singapore (SG)

(73) Assignee: National University of Singapore, Singapore (SG)

(*) Notice: Subject to any disclaimer, the term of this patent is extended or adjusted under 35 U.S.C. 154(b) by 0 days.

(21) Appl. No.: 13/156,782

(22) Filed: Jun. 9, 2011

(65) Prior Publication Data

US 2012/0028269 A1 Feb. 2, 2012

Related U.S. Application Data

(60) Provisional application No. 61/397,299, filed on Jun. 10, 2010.

(51) Int. Cl.
*G01N 33/573* (2006.01)
*G01N 33/574* (2006.01)

(52) U.S. Cl.
CPC ... *G01N 33/57446* (2013.01); *G01N 2333/811* (2013.01); *G01N 2800/50* (2013.01); *G01N 2800/52* (2013.01); *G01N 2800/54* (2013.01)

(58) Field of Classification Search
None
See application file for complete search history.

(56) References Cited

U.S. PATENT DOCUMENTS

| | | |
|---|---|---|
| 2008/0311567 A1 | 12/2008 | Bruckl et al. |
| 2010/0273148 A1 | 10/2010 | Guilford et al. |
| 2010/0285507 A1 | 11/2010 | Cho et al. |

FOREIGN PATENT DOCUMENTS

| | | |
|---|---|---|
| WO | WO 2007/122369 A2 | 11/2007 |
| WO | WO 2010/040571 A2 | 4/2010 |
| WO | WO 2010/045714 A1 | 4/2010 |
| WO | WO 2010/127399 A1 | 11/2010 |

OTHER PUBLICATIONS

Hamm et al BMC Cancer 8:25 published 2008.*
Chong et al, J proteome Res 9:3671-3679, online published Jun. 1, 2012.*
Heo et al Proteomics, 7: 4292-4302, 2007.*
Abdulla-Soheimi, S.S., et al., "Patients with Ovarian Carcinoma Excrete Different Altered Levels of Urine CD59, Kininogen-1 and Fragments of Inter-Alpha-Trypsin Inhibitor Heavy Chain H4 and Albumin", *Proteome Science*, 8(58): 7 pages (2010).
Cerwenka, H. et al., "TUM2-PK (Pyruvate Kinase Type Tumor M2), CA19-9 and CEA in Patients with Benign, Malignant and Metastasizing Pancreatic Lesions", *Anticancer Res*, 19:849-851 (1999).
Chattelji, B. and Borlak, J., "A 2-DE MALDI-TOF Study to Identify Disease Regulated Serum Proteins in Lung Cancer of C-MYC Transgenic Mice", *Proteomics*, 9:1044-1056 (2009).
Chong, P.K., et al., ITIH3 is a Potential Biomarker for Early Detection of Gastric Cancer, *J Proteome Res*, 9:3671-3679 (2010).
Chong, P.L., et al., "Reduced Plasma APOA1 Level is Associated With Gastric Tumor Growth in MKN45 Mouse Xenograft Model", *J. Proteomics*, 73:1632-1640 (2010).
Chong, P.K., et al., "Upregulation of Plasma C9 Protein in Gastric Cancer Patients", *Proteomics*, 10: 3210-3221 (2010).
Dinis-Ribeiro, M. et al., "Meta-Analysis on the Validity of Pepsinogen Test for Gastric Carcinoma, Dysplasia or Chronic Atrophic Gastritis Screening", *J Med Screen*, 11(3): 141-147 (2004).
Ebert, M. P. and Röcken, C., "Molecular Screening of Gastric Cancer by Proteome Analysis", *Eur J Gastroenterol & Hepatol*, 18: 847-853 (2006).
Hamm, A., et al., "Freqeuent Expression Loss of Inter-Alpha-Trypsin Inhibitor Heavy Chain (ITIH) Genes in Multiple Human Solid Tumors: A Systematic Expression Analysis", *BMC Cancer*, 8(25): 15 pages (2008).
Hardt, P. D., et al., "Tumor M2-Pyruvate Kinase: A Promising Tumor Marker in the Diagnosis of Gastro-Intestinal Cancer", *Anticancer Res*, 20: 4965-4968 (2000).
Heo, S. H. et al., "Identification of Putative Serum Glycoprotein Biomarkers for Human Lung Adenocarcinoma by Multilectin Affinity Chromatography and LC-MS/MS", *Proteomics* 7: 4292-4302 (2007).
Huang, L. et al., "Activity of Calf Thymus DNA Helicase E on cis-Diamminedichloroplatinum (II)-Damaged DNA*", *J Biol Chem*, 268(35): 26731-26737 (1993).
Ichikawa, D., et al., "Detection of Aberrant Methylation as a Tumor Marker in Serum of Patients with Gastric Cancer", *Anticancer Research*, 24: 2477-2481 (2004).
Kanyama, Y., et al., "Detection of p16 Promoter Hypermethylation in Serum of Gastric Cancer Patients", *Cancer Science*, 94(5): 418-420 (2003).
Kobayashi, H. et al., "Inhibitory Effect of a Conjugate Between Human Urokinase and Urinary Trypsin Inhibitor on Tumor Cell Invasion in Vitro*", *J Biol Chem*, 270 (14): 8361-8366 (1995).
Kobayashi, H. et al., "Inhibition of Metastasis of Lewis Lung Carcinoma by Urinary Trypsin Inhibitor in Experimental and Spontaneous Metastasis Models", *Int J Cancer*, 63:455-462 (1995).
Miki, K., et al., "Long-Term Results of Gastric Cancer Screening Using the Serum Pepsinogen Test Method Among an Asymptomatic Middle-Aged Japanese Population", *Digestive Endoscopy*, 21:78-81 (2009).
Paris, S,. et al., "Inhibition of Tumor Growth and Metastic Spreading by Overexpression of Inter-Alpha-Trypsin Inhibitor Family Chains", *Int J Cancer*, 97: 615-620 (2002).

(Continued)

*Primary Examiner* — Lei Yao
(74) *Attorney, Agent, or Firm* — Scully Scott Murphy & Presser

(57) ABSTRACT

The invention is directed to non-invasive methods of detecting gastric cancer in an individual in need thereof comprising determining an expression level of inter-alpha-trypsin inhibitor heavy chain H3 (ITIH3) in the individual and comparing the expression level to a control, wherein an increase in the expression level of ITIH3 in the individual compared to the control is indicative of gastric cancer in the individual.

6 Claims, 14 Drawing Sheets

(56) References Cited

OTHER PUBLICATIONS

Qiao, S.X., et al., "Detection of Gastric Cancer and Premalignant Lesions by Novel Marker Glycoprotein 87 Using Monoclonal Antibody Adnab-9", *Cancer Epidemiol Biomarkers Prev.* 12: 1095-1099 (2003).

Song, J., et al., "Quantification of Fragments of Human Serum Inter-Alpha-Trypsin Inhibitor Heavy Chain 4 by a Surface-Enhanced Laser Desorption/Ionization-Based Immunoassay", *Clinical Chemistry*, 52(6): 1045-1053 (2006).

Veeck, J. et al., "Novel Prognostic Marker in Invasive Breast Cancer. ITIH5 Expression is Abrogated by Aberrant Promoter Methylation", *Pathologe* 2008, 29(Supp 12): 338-346 (2008).

Veeck, J. et al. "The Extracellular Matrix Protein ITIH5 is a Novel Prognostic Marker in Invasive Node-Negative Breast Cancer and its Aberrant Expression is Caused by Promoter Hypermethylation", *Oncogene*, 27: 865-876 (2008).

Wantanabe, Y., et al., "Sensitive and Specific Detection of Early Gastric Cancer With DNA Methylation Analysis of Gastric Washes", *Gastroenterology*, 136(7): 2149-2158 (2009).

Zhuo, L. et al., "Inter-α-Trypsin Inhibitor, a Covalent Protein-Glycosaminoglycan-Protein Complex*", *J Biol Chem*, 279(37): 38079-38082 (2004).

\* cited by examiner

| A | Expression trend | No of cases | Percentage (%) |
|---|---|---|---|
| | T > N | 4/19 | 21 |
| | T = N | 8/19 | 42 |
| | T < N | 5/19 | 26 |
| | No scoring | 2/19 | 11 |

Figure 5A

Normal tissue          Tumor tissue

```
              10          20          30          40          50          60
     MAFAWWPCLI  LALLSSLAAS  GFPRSPFRLL  GKRSLPEGVA  NGIEVYSTKI  NSKVTSRFAH 70          80          90         100         110         120
     NVVTMRAVNR  ADTAKEVSFD  VELPKTAFIT  NFTLTIDGVT  YPGNVKEKEV  AKKQYEKAVS 130         140         150         160         170         180
     QGKTAGLVKA  SGRKLEKFTV  SVNVAAGSKV  TFELTYEELL  KRHKGKYEMY  LKVQPKQLVK 190         200         210         220         230         240
     HFEIEVDIFE  PQGISMLDAE  ASFITNDLLG  SALTKSFSGK  KGHVSFKPSL  DQQRSCPTCT 250         260         270         280         290         300
     DSLLNGDFTI  TYDVNRESPG  NVQIVNGYFV  HFFAPQGLPV  VPKNVAFVID  ISGSMAGRKL 310         320         330         340         350         360
     EQTKEALLRI  LEDMQEEDYL  NFILFSGDVS  TWKEHLVQAT  PENLQEARTF  VKSMEDKGMT 370         380         390         400         410         420
     NINDGLLRGI  SMLNKAREEH  RIPERSTSIV  IMLTDGDANV  GESRPEKIQE  NVRNAIGGKF 430         440         450         460         470         480
     PLYNLGFGNN  LNYNFLENMA  LENHGFARRI  YEDSDADLQL  QGFYEEVANP  LLTGVEMEYP 490         500         510         520         530         540
     ENAILDLTQN  TYQHFYDGSE  IVVAGRLVDE  DMNSFKADVK  GHGATNDLTF  TEEVDMKEME 550         560         570         580         590         600
     KALQERDYIF  GNYIERLWAY  LTIEQLLEKR  KNAHGEEKEN  LTARALDLSL  KYHFVTPLTS 610         620         630         640         650         660
     MVVTKPEDNE  DERAIADKPG  EDAEATPVSP  AMSYLTSYQP  PQNPYYYVDG  DPHFIIQIPE 670         680         690         700         710         720
     KDDALCFNID  EAPGTVLRLI  QDAVTGLTVN  GQITGDKRGS  PDSKTRKTYF  GKLGIANAQM
```

Figure 6A

```
              730        740        750        760        770        780
        DFQVEVTTEK ITLWNRAVPS TFSWLDTVTV TQDGLSMMIN RKNMVVSFGD GVTFVVVLHQ 790        800        810        820        830        840
        VWKKHPVHRD FLGFYVVDSH RMSAQTHGLL GQFFQPFDFK VSDIRPGSDP TKPDATLVVK 850        860        870        880        890
        NHQLIVTRGS QKDYRKDASI GTKVVCWFVH NNGEGLIDGV HTDYIVPNLF
```

Figure 6B

METHODS FOR DETECTION OF GASTRIC CANCER

RELATED APPLICATION(S)

This application claims the benefit of U.S. Provisional Application No. 61/397,299, filed on Jun. 10, 2010. The entire teachings of the above application are incorporated herein by reference.

BACKGROUND OF THE INVENTION

Gastric cancer is the second leading cause of cancer-related deaths worldwide and early detection is the key in its management. Endoscopy is widely used for screening; however this methodology involves invasive procedure and its cost effectiveness remains an issue. One of the main goals in molecular biomarker discovery today is to develop a non/minimally-invasive method for cancer screening. In clinical diagnosis, body fluids especially plasma, serum and urine are frequently sampled from patients since they are easily obtained without complicated procedures. Hence, they represent ideal substrates for diagnostic purposes. However biomarker discovery in body fluid is not without challenges. The wide dynamic range of more than 9 orders of magnitude in protein concentration coupled with 20 abundant proteins accounting for 99% of total protein mass has hindered the detection of low abundance proteins (Anderson, N. L.; Anderson, N. G., *Mol Cell Proteomics* 2002, 1, (11), 845-67).

A need exists for improved, non-invasive methods for detection of gastric cancer.

SUMMARY OF THE INVENTION

Gastric cancer has one of the highest morbidities and mortalities worldwide. Early detection is a key measure to improve the outcome of gastric cancer patients The present invention is directed to non-invasive methods of detecting gastric cancer. In one aspect, the invention is directed to a method of detecting gastric cancer in an individual in need thereof (e.g., a symptomatic individual; an asymptomatic individual) comprising determining an expression level of inter-alpha-trypsin inhibitor heavy chain H3 (ITIH3) in the individual and comparing the expression level to a control, wherein an increase in the expression level of ITIH3 in the individual compared to the control is indicative of gastric cancer in the individual.

In another aspect, the invention is directed to a method of detecting early stage gastric cancer in an individual in need thereof comprising determining an expression level of inter-alpha-trypsin inhibitor heavy chain H3 (ITIH3) in the individual and comparing the expression level to a control, wherein an increase in the expression of ITIH3 in the individual compared to the control is indicative of early stage gastric cancer in the individual.

In yet another aspect, the invention is directed to a method of detecting an individual at risk for developing gastric cancer comprising determining an expression level of inter-alpha-trypsin inhibitor heavy chain H3 (ITIH3) in the individual compared to a control, wherein an increase in the expression level of ITIH3 in the individual compared to the control is indicative of an individual at risk for developing gastric cancer.

The invention is also directed to a method of detecting recurrence of gastric cancer in an individual in need thereof comprising determining an expression level of inter-alpha-trypsin inhibitor heavy chain H3 (ITIH3) in the individual compared to a control, wherein an increase in the expression level of ITIH3 in the individual compared to the control is indicative of recurrence of gastric cancer in the individual.

Another aspect of the invention is a method of monitoring a treatment for gastric cancer in an individual in need thereof comprising determining an expression level of inter-alpha-trypsin inhibitor heavy chain H3 (ITIH3) in the individual compared to a control, wherein if the expression level of ITIH3 is similar, or decreased, in the individual compared to the control, then the treatment is effective, and if the expression level of ITIH3 in the individual is increased compared to the control, then the treatment is not effective.

In yet another aspect the invention is directed to a method of distinguishing a benign gastric disease from a malignant gastric disease in an individual in need thereof (e.g., a symptomatic individual, an asymptomatic individual). The method comprises determining an ITIH3 expression level in the individual, wherein an increase in the expression level of ITIH3 in the individual compared to the control is indicative of a malignant gastric disease in the individual. Conversely, an expression level that is similar to, or decreased, in the individual compared to the control level is indicative of a benign gastric disease in the individual.

BRIEF DESCRIPTION OF THE DRAWINGS

FIG. 5A is a summary table of IHC results of ITIH3 expression level obtained from 19 match tumor and normal cases. The abbreviation 'T' and 'N' indicate tumor and normal tissue.

FIGS. 6A-6B shows the amino acid sequence of human ITIH3.

DETAILED DESCRIPTION OF THE INVENTION

Figure 1:
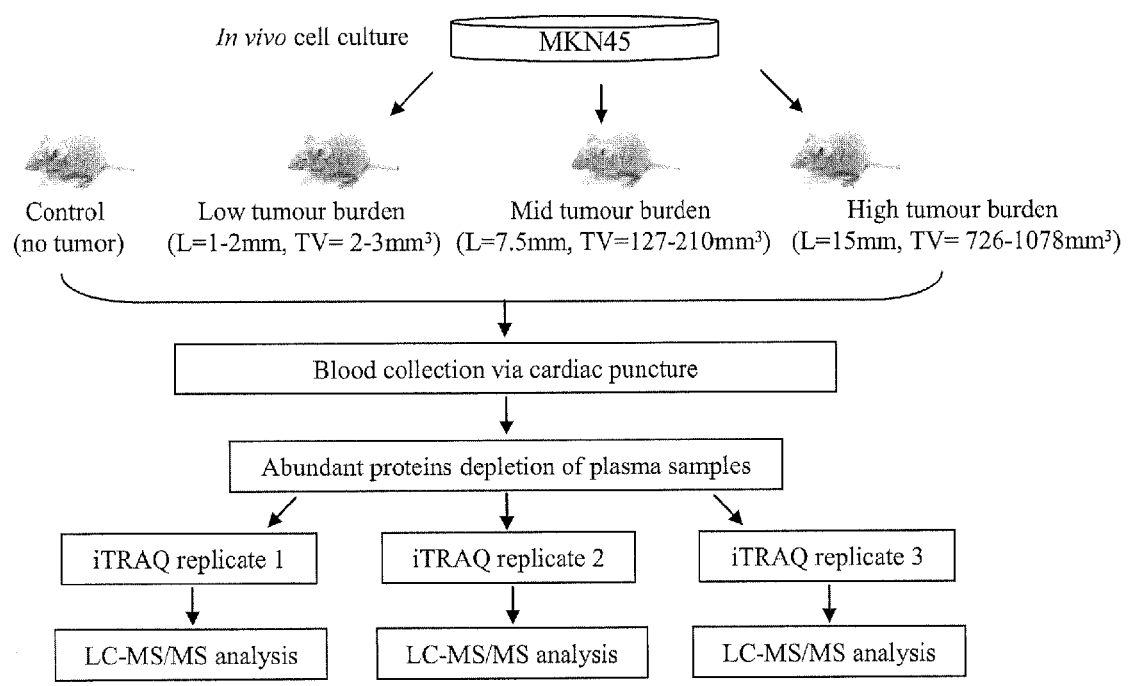
FIG. 1 is a schematic of an overview of the workflow employed in this study. Three iTRAQ™ replicates were carried out to ensure the consistency and reliability in results.

A mouse xenograft model is an alternative to analysis of clinical samples for biomarker discovery. It presents less genetic and biological variations compared to a human model at the same time allowing environmental factor to be tightly controlled (Frese, K K.; Tuveson, D. A., *Nat Rev Cancer* 2007, 7, (9), 645-58). Another advantage is that the xenograft model tends to have bigger tumor/blood ratio than humans, thereby enabling easier detection of cancer-induced changes. The feasibility of using a xenograft model for biomarker discovery had been demonstrated by various serum biomarker studies including that for breast (Pitteri, S. et al., *J Proteome Res* 2008, 7, (4), 1481-9), pancreas (Faca, V. M. et al., *PLoS Med* 2008, 5, (6), e123), stomach (Juan, H. F. et al., *Proteomics* 2004, 4, (9), 2766-75) and prostate (van Weerden, W. M.; Romijn, J. C., *Prostate* 2000, 43, (4), 263-71). For example, identification of nm23/nucleoside-diphosphate kinase and human glycolytic enzyme in prostate cancer mouse xenograft has been achieved (van Weerden, W. M.; Romijn, J. C., *Prostate* 2000, 43, (4), 263-71). Another study on nasopharyngeal carcinoma identified peroxiredoxin 2 up-regulation in the plasma of tumor-bearing compared to control mice and subsequent ELISA screening on clinical samples showed the similar observation (Wu, C. C. et al., *Proteomics* 2008, 8, (17)).

Described herein is the utilization of the Isobaric Tags for Relative and Absolute Quantification (iTRAQ™) approach to profile the levels of proteins in the plasma from control mice and mice bearing different sizes of MKN45 gastric cancer cell line-derived tumors. As also described herein, protein candidates were identified in mice and the selected candidate was validated in human samples. See Chong, P. K., et al., *J Proteome Res*, 2010, 9:3671-3679 which is incorporated herein by reference.

Specifically, a xenotransplantation mouse model was coupled with a plasma proteomic approach to identify potential markers for gastric cancer detection. MKN45 gastric cancer cells were subcutaneously injected into nude mice and plasma samples from mice bearing different sizes of tumors were collected and subjected to iTRAQ™ (Applied Biosystems) and mass spectrometry analysis. Inter-alpha-trypsin inhibitor heavy chain 3 (ITIH3) protein was found to be highly expressed in plasma of tumor bearing mice compared to control. Subsequent screening of ITIH3 expression in 167 clinical plasma samples, including 83 normal (cancer free) subjects and 84 gastric cancer patients, revealed higher ITIH3 expression levels in the plasma of gastric cancer patients. A receiver operating characteristics (ROC) curve generated from the screening of 167 clinical samples estimated ITIH3 specificity and sensitivity of 66% and 96% respectively, for gastric cancer detection. In addition, plasma from early stage gastric cancer patients had a significantly (p<0.001) higher level of ITIH3 compared to that from non-cancer subjects. ITIH3 is shown herein to be a useful biomarker for detection of gastric cancer.

Accordingly, the invention is directed to non-invasive methods of detecting gastric cancer. In one aspect, the invention is directed to a method of detecting gastric cancer in an (one or more) individual in need thereof (e.g., a symptomatic individual; an asymptomatic individual) comprising (consisting essentially of; consisting of) determining an expression level of inter-alpha-trypsin inhibitor heavy chain H3 (ITIH3) in the individual and comparing the expression level to a control, wherein an increase in the expression level of ITIH3 in the individual compared to the control is indicative of gastric cancer in the individual.

As used herein ITIH3 is one of the five heavy chains (ITIH1, ITIH2, ITIH3, ITIH4 and ITIH5) belonging to the family of inter-alpha-trypsin inhibitor, comprising a family of protease inhibitors that are found in the extracellular matrix of various organs including blood. One of the well-known functions of these heavy chains is the ability to link covalently to hyaluronic acid (HA), a major component of extracellular matrix (Huang, L. et al., *J Biol Chem* 1993, 268). FIGS. 6A-6B show the amino acid sequence of human ITIH3, see also ITIH3 HUMAN, Q06033.

As shown herein, the expression level of ITIH3 can be used to detect various stages of gastric cancer in an individual. The stage of gastric cancer is an indication of how advanced the cancer is. Based on the American Joint Committee on Cancer (AJCC), early stage gastric cancer is generally referred to as Stage I or Stage II, and later stage gastric cancer is generally referred to as Stage III or Stage IV.

As used herein an "individual" refers to any subject in need of screening. In particular embodiments, the individual is a mammal, such as a primate (e.g., human), cow, sheep, goat, horse, dog, cat, rabbit, guinea pig, rat, mouse or other bovine, ovine, equine, canine feline, rodent or murine species. In one embodiment, the individual is a human. In another embodiment, the individual is not a cancer patient (e.g., not a gastric cancer patient) or is not known to have cancer (e.g., gastric cancer). In other embodiments, the individual is a cancer patient (e.g., a gastric cancer patient)). In some embodiments, the individual is a gastric cancer patient that has not been treated. In other embodiments, the individual is a gastric cancer patient that has had, or is undergoing, treatment (e.g., chemotherapy, surgery). In yet another embodiment, the individual is in remission from gastric cancer.

As described herein, the method comprises detecting the expression level of ITIH3 in the individual, such as in a sample from an individual. Detection of the expression level of ITIH3 can be achieved using a variety of methods. For example, ITIH3 can be detected using DNA techniques such as gel electrophoresis (e.g., agarose gel), real time PCR, DNA microarray or protein-based methods such as high-resolution denaturing polyacrylamide/urea gel electrophoresis, capillary separation, ELISA, mass spectrometry, use of aptamers or other resolving and/or immunological means.

More specifically, as will be appreciated by those of skill in the art, expression levels of ITIH3 can be detected, directly or indirectly, using a variety of methods known in the art. For example, ITIH3 nucleic acid or a (one or more) portion thereof, ITIH3 protein or a (one or more) portion thereof, ITIH3 activity and combinations thereof can be detected using a variety of appropriate methods, including for example, methods for detecting the quantity of ITIH3 mRNA transcribed from the ITIH3 gene, the quantity of cDNA produced from the reverse transcription of the mRNA transcribed from the ITIH3 gene, the quantity of the ITIH3 polypeptide or protein encoded by the ITIH3 gene, or the activity of the ITIH3 polypeptide or protein encoded by the ITIH3 gene. In particular embodiments, the expression level of ITIH3 protein is detected.

Such methods can be performed on a sample by sample basis or modified for high throughput analysis. As indicated in more detail below, samples used for this invention encompass body fluid, solid tissue samples, tissue cultures or cells derived therefrom and the progeny thereof and sections or smears prepared from any of these sources or any other samples that may contain a cell having a ITIH3 gene described herein.

In assaying for ITIH3 polypeptide, an ITIH3 polypeptide (also referred to herein as a protein) or a portion thereof can be detected. As will be appreciated by those of skill in the art, the portion of ITIH3 that can be detected in the methods can be a a full length ITIH3 protein or a portion of a ITIH3 protein (ITIH3 peptide or polypeptide) such as a portion of ITIH3 which has ITIH3 activity (e.g., a biologically active portion or ITIH3) a portion of ITIH3 which does not have ITIH3 activity. In one aspect, the portion of ITIH3 detected in the methods is a biologically active portion of a ITIH3 poplypeptide.

As used herein, a "biologically active portion of an ITIH3 polypeptide" is a portion of an ITIH3 polypeptide that retains one or more functions and/or activities of ITIH3. Functions of ITIH3 include protease inhibitor activity and the ability to link covalently to hyaluronic acid.

In assaying for an expression level of an ITIH3 polypeptide or portion thereof, a variety of techniques are available in the art. They include but are not limited to radioimmunoassays, ELISA (Enzyme Linked Immunoradiometric Assays), "sandwich" immunoassays, immunoradiometric assays, in situ immunoassays (using e.g., colloidal gold, enzyme or radioisotope labels), western blot analysis, immunoprecipitation assays, immunofluorescent assays, PAGE-SDS and protein chips. One means to determine an expression level of ITIH3 involves (a) providing a biological sample containing ITIH3 polypeptide(s); and (b) measuring the amount of any immunospecific binding that occurs between an antibody reactive (specifically reactive) to the ITIH3 polypeptide or portion thereof and the ITIH3 polypeptide or portion thereof in the sample, in which the amount of immunospecific binding indicates the expression level of the ITIH3 polypeptide(s) in the sample.

Antibodies that specifically recognize and bind to an ITIH3 polypeptide or portion thereof are used in immunoassays. Such antibodies may be purchased from commercial vendors (R&D Systems, Abcam, and Santa Cruz Biotechnology) or generated and screened using methods well known in the art. Alternatively, polyclonal or monoclonal antibodies that specifically recognize and bind the protein product of a gene of interest can be made and isolated using known methods. See, for example, Molecular Cloning: A Laboratory Manual, second edition (Sambrook et al., 1989) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2001); Harlow and Lane (1988) Antibodies, A Laboratory Manual, Cold Spring Harbor Publications, New York; Harlow and Lane (1999) Using Antibodies: A Laboratory Manual Cold Spring Harbor Laboratory Press, Cold Spring Harbor, N.Y. (jointly referred to herein as "Harlow and Lane").

An antibody that is specific for ITIH3 or portion thereof is a molecule that selectively binds to ITIH3 but does not substantially bind to other molecules in a sample, e.g., in a biological sample that contains ITIH3. The term "antibody," as used herein, refers to an immunoglobulin or a part thereof, and encompasses any polypeptide comprising an antigen-binding site regardless of the source, method of production, and other characteristics. The term includes but is not limited to polyclonal, monoclonal, monospecific, polyspecific, humanized, human, single-chain, chimeric, synthetic, recombinant, hybrid, mutated, conjugated and CDR-grafted antibodies. The term "antigen-binding site" or "antigen binding fragment" refers to the part of an antibody molecule that comprises the area specifically binding to or complementary to, a part or all of an antigen. An antigen-binding site may comprise an antibody light chain variable region (VL) and an antibody heavy chain variable region (VH). An antigen-binding site may be provided by one or more antibody variable domains (e.g., an Fd antibody fragment consisting of a VH domain, an Fv antibody fragment consisting of a VH domain and a VL domain, or an scFv antibody fragment consisting of a VH domain and a VL domain joined by a linker). The term "anti-ITIH3 antibody," or "antibody against ITIH3," refers to any antibody that specifically binds to at least one epitope of ITIH3. As used herein, the term "selectively binds to" or "binding specificity" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. In particular aspects, the invention is directed to an antibody that has binding specificity (e.g., epitopic specificity) for all or a portion of a ITIH3 polypeptide.

The various antibodies and portions thereof can be produced using known techniques (Kohler and Milstein, Nature 256:495-497 (1975); Current Protocols in Immunology, Coligan et al., (eds.) John Wiley & Sons, Inc., New York, N.Y. (1994); Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1; Newman, R. et al., BioTechnology, 10: 1455-1460 (1992); Ladner et al., U.S. Pat. No. 4,946,778; Bird, R. E. et al., Science, 242: 423-426 (1988)).

As noted above, antibodies useful in the present invention can include polyclonal and monoclonal antibodies, divalent and monovalent antibodies, bi- or multi-specific antibodies, serum containing such antibodies, antibodies that have been purified to varying degrees, and any functional equivalents of whole antibodies. Isolated antibodies of the present invention can include serum containing such antibodies, or antibodies that have been purified to varying degrees. Alternatively, functional equivalents of whole antibodies, such as antigen binding fragments in which one or more antibody domains are truncated or absent (e.g., Fv, Fab, Fab', or F(ab)2 fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Genetically engineered antibodies include those produced by standard recombinant DNA techniques involving the manipulation and re-expression of DNA encoding antibody variable and/or constant regions. Particular examples include, chimeric antibodies, where the VH and/or VL domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Constructions of chimeric and CDR-grafted antibodies are described, for example, in European Patent Applications: EP-A 0194276, EP-A 0239400, EP-A 0451216 and EP-A 0460617. Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (Nature 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

In addition, or in the alternative, ITIH3 nucleic acid or portion thereof can be detected in the methods of the invention. In one embodiment of assaying for ITIH3 nucleic acid or portion thereof, nucleic acid contained in the individual (e.g., a sample of the individual) is first extracted according to standard methods in the art. For instance, nucleic acid can be isolated using various lytic enzymes or chemical solutions according to the procedures set forth, for example, in Methods of Enzymology, Vol. 194, Guthrie et al., eds., Cold Spring Harbor Laboratory Press (1990); Molecular Cloning: A Laboratory Manual, second edition (Sambrook et al., 1989) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2001. The mRNA of a gene contained in the extracted nucleic acid sample is then detected by hybridization (e.g., Northern blot analysis) and/or amplification procedures according to methods widely known in the art or based on the methods exemplified herein (e.g., PCR: The Polymerase Chain Reaction, (Mullis et al., eds., 1994)).

Nucleic acid molecules exhibiting sequence complementarity or homology to an ITIH3 polynucleotide or portion thereof are useful as hybridization probes. It is known in the art that a "perfectly matched" probe is not needed for a specific hybridization. Minor changes in probe sequence achieved by substitution, deletion or insertion of a small number of bases do not affect the hybridization specificity. These probes can be used in radioassays (e.g., Southern and Northern blot analysis) to detect ITIH3 nucleic acid. In one aspect, nucleotide probes having complementary sequences over stretches greater than about 10 nucleotides in length are used, so as to increase stability and selectivity of the hybrid and, thereby, improving the specificity of particular hybrid molecules obtained. Alternatively, one can design nucleic acid molecules having gene-complementary stretches of more than about 25 or alternatively more than about 50 nucleotides in length or even longer where desired. Such fragments may be readily prepared by, for example, directly synthesizing the fragment by chemical means, by application of nucleic acid reproduction technology, such as the PCRTM technology with two priming oligonucleotides as described in U.S. Pat. No. 4,603,102 or by introducing selected sequences into recombinant vectors for recombinant production. In one aspect, a probe is about 50 to about 75, nucleotides or, alternatively, about 50 to about 100 nucleotides in length. These probes can be designed from the sequence of full length genes. In certain embodiments, it will be advantageous to employ nucleic acid sequences as described herein in combination with an appropriate means, such as a label, for detecting hybridization and therefore complementary sequences. A wide variety of appropriate indicator means are known in the art, including fluorescent, radioactive, enzymatic or other ligands, such as avidin/biotin, which are capable of giving a detectable signal. One can employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

Hybridization reactions can be performed under conditions of different "stringency". Relevant conditions include temperature, ionic strength, time of incubation, the presence of additional solutes in the reaction mixture such as formamide and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. See, for example, Sambrook et al. supra.

Known amplification methods include PCR, MacPherson et al., PCR: A PRACTICAL APPROACH, (IRL Press at Oxford University Press (1991)). However, PCR conditions used for each application reaction are empirically determined. A number of parameters influence the success of a reaction. Among them are annealing temperature and time, extension time, $Mg^{2+}$ ATP concentration, pH and the relative concentration of primers, templates and deoxyribonucleotides.

After amplification, the resulting DNA fragments can be detected by agarose gel electrophoresis followed by visualization with ethidium bromide staining and ultraviolet illumination. A specific amplification of differentially expressed genes of interest can be verified by demonstrating that the amplified DNA fragment has the predicted size, exhibits the predicated restriction digestion pattern and/or hybridizes to the correct cloned DNA sequence.

Probes also can be attached to a solid support for use in high throughput screening assays using methods known in the art. PCT WO 97/10365 and U.S. Pat. Nos. 5,405,783; 5,412,087 and 5,445,934; for example, disclose the construction of high density oligonucleotide chips which can contain one or more of the sequences that hybridize to an ITIH3 sequence.

The expression level of a gene can also be determined through exposure of a nucleic acid sample to a probe-modified chip. Extracted nucleic acid is labeled, for example, with a fluorescent tag, preferably during an amplification step. Hybridization of the labeled sample is performed at an appropriate stringency level. The degree of probe-nucleic acid hybridization is quantitatively measured using a detection device, such as a confocal microscope. See, U.S. Pat. Nos. 5,578,832 and 5,631,734. The obtained measurement is directly correlated with gene expression level.

For detection purposes, the agent that specifically recognizes expression of ITIH3 (e.g., an antibody that specifically binds ITIH3) can comprise at least one tag or label. As used herein, "tag" or "label" are used interchangeably to refer to any moiety that is capable of being specifically detected (e.g., by a partner moiety), either directly or indirectly, and therefore, can be used to identify and/or isolate a polynucleotide sequence that comprises the tag. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein and the like), radiolabels (e.g., 3H, 125I, 35S, 14C or 32P) enzymes (e.g., horseradish peroxidase, alkaline phosphatase and others commonly used in an ELISA) and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Other suitable tags for the present invention include, among others, affinity tags (e.g., biotin, avidin, streptavidin), haptens, ligands, peptides, nucleic acids, fluorophores, chromophores, and epitope tags that are recognized by an antibody (e.g., digoxigenin (DIG), hemagglutinin (HA), myc, Flag) (Andrus, A. "Chemical methods for 5' non isotopic labelling of PCR probes and primers" (1995) in PCR 2: A Practical Approach, Oxford University Press, Oxford, pp. 39 54). Other suitable tags include, but are not limited to, chromophores, fluorophores, haptens, radionuclides (e.g., 32P, 33P, 35S), fluorescence quenchers, enzymes, enzyme substrates, affinity tags (e.g., biotin, avidin, streptavidin, etc.), mass tags, electrophoretic tags and epitope tags that are recognized by an antibody.

Means of detecting such labels are known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate and colorimetric labels are detected by simply visualizing the colored label.

In addition, or in the alternative, ITIH3 activity can be detected in the methods of the invention. In assaying for ITIH3 activity a variety of methods known to those of skill in the art are also available for use in the methods of the invention. For example, ITIH3 protease inhibition activity or hyaluronic acid binding activity can be detected.

In the methods of the present invention, the expression level of ITIH3 in the individual can be determined from a sample (a test sample) of the individual. Thus, the methods can further comprise obtaining a (one or more) sample from an (one or more) individual. For example, a sample includes tissues, cells, biological fluids and extracts thereof obtained (e.g., isolated) from an individual as well as present in an individual. Although plasma has been shown herein to be a suitable sample, one of skill in the art will appreciate that any suitable biological sample obtained from an individual can be used in the methods of the invention to detect the expression of ITIH3 in an individual. The sample can be a biological fluid, a tissue sample (e.g., gastric tissue), a tumor sample (e.g., a gastric tumor) and combinations thereof. A suitable sample can be obtained for example by cell or tissue biopsy. A sample can also be obtained from other tissues, bodily fluids and products, e.g., from a tissue smear, tissue scrape, and the like. Thus, the sample can be a biopsy specimen (e.g, tumor, polyp, mass (solid, cellular)), aspirate, and/or smear sample). The sample can be from a tissue that has a tumor (e.g., cancerous growth) and/or tumor cells, or is suspected of having a tumor and/or tumor cells. For example, a tumor biopsy can be obtained in an open biopsy, a procedure in which an entire (excisional biopsy) or partial (incisional biopsy) mass is removed from a target area. Alternatively, a tumor sample can be obtained through a percutaneous biopsy, a procedure performed with a needle-like instrument through a small incision or puncture (with or without the aid of a imaging device) to obtain individual cells or clusters of cells (e.g., a fine needle aspiration (FNA)) or a core or fragment of tissues (core biopsy).

In a particular embodiment, the sample is a biological fluid. Examples of a biological fluid that can be used in the methods include plasma, blood (e.g., whole blood, packed red blood cells), urine, lymph and the like. In a particular aspect, the sample is plasma.

The level of ITIH3 can also be detected in the individual without the need to remove or obtain a sample from the individual. That is, in the methods of the present invention, the expression level of ITIH3 of an individual can be detected (directly, indirectly) in vitro or in vivo. Examples of in vitro and in vivo techniques for detection of expression levels of proteins such as ITIH3 (e.g., in a sample) are known in the art. Such in vitro methods include electrophoresis methods (e.g., polyacyrlamise gel electrophoresis such as SDS-PAGE), mass spectrometry methods (e.g., electrospray ionization mass spectrometry (ESI-MS), liquid chromatography-mass spectrometry (LC-MS), fast atom bombardment tandem mass spectrometry); chromatography methods (e.g., high performance liquid chromatography (HPLC), gas chromatography (GC)); ultraviolet (UV) methods; immunoassay methods (e.g., immunoprecipitations, immunofluorescence); enzymatic assays (e.g., colorimetric assays) and combinations thereof.

Examples of in vivo techniques for detection of proteins such as ITIH3 (e.g., in an individual) include in vivo fluorescence imaging using fluorescent dye-tagged antibodies, e.g., injected into an individual's circulation.

A sample obtained from an individual can be stored, analyzed immediately or processed prior to detection of expression levels of ITIH3, and depends upon the type of sample and the method of detection used to determine the expression level of ITIH3 in the sample.

The level of ITIH3 expression in an (one or more) individual or a sample from an individual can be determined qualitatively and/or quantitatively. In one embodiment, the level of ITIH3 expression in the tested individual or sample can be compared to the level of ITIH3 in a control. For example, an expression level of ITIH3 in the individual or sample that is higher (increased) than the expression level of ITIH3 in a control (e.g., control individual or control sample) is indicative of gastric cancer in the individual. Any suitable control sample can be used, wherein the expression level of ITIH3 in the control sample is indicative of the expression level of ITIH3 in an individual (one or more) that does not have gastric cancer (e.g., the level of ITIH3 in one or more healthy individuals). Suitable controls are well recognized in the art and include, for example, a sample from an individual that does not have gastric cancer, a sample from an individual that does have gastric cancer, a sample from an individual that is a gastric cancer patient, and/or a reference standard of authentic (positive) ITIH3. The control sample can be the same type of sample as the sample obtained from the individual (e.g., the sample obtained from the individual and the control sample are plasma samples) or the control sample can be a different sample (e.g., the sample obtained from the individual is a plasma sample and the control sample is a tissue sample such as a gastric tissue sample). In particular embodiments, a suitable control can be established by assaying a large sample of individuals which do not have gastric cancer and using a statistical model to obtain a control value (standard value). See, for example, models described in Knapp, R. G. and Miller M. C. (1992) Clinical Epidemiology and Biostatistics, William and Wilkins, Harual Publishing Co. Malvern, Pa., which is incorporated herein by reference.

Thus, as will be appreciated by those of skill in the art, the control sample can be an actual sample or it can be a value or range of values (e.g., from a control population) previously determined. For example, the control sample can be derived from a subject that lacks the clinical characteristics of gastric cancer, referred to herein as a "normal control" or "negative control". Examples of such controls includes one or more samples from one or more healthy individuals, a reference standard (e.g., using purified recombinant or native ITIH3 (e.g., human ITIH3)) or a combination thereof. A lack of correlation between the subject and the negative control indicates that the individual is afflicted with gastric cancer.

In the alternative, or in addition, the method can also include a control sample derived from a subject (hereinafter "positive control"), that exhibits gastric cancer. A positive correlation between the subject and the positive control indicates that the individual is afflicted with gastric cancer.

In the methods provided herein, gastric cancer or the risk of gastric cancer is determined when the expression level of ITIH3 is increased (greater than, higher) compared to the expression level of ITIH3 in a suitable control. In some embodiments, an increased expression level of ITIH3 is about 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.5, 6.0, 6.5, 7.0, 7.5, 8.0, 8.5, 9.0, 9.5 or 10 fold higher than the expression level of ITIH3 in a suitable control. In a particular embodiment, an increased expression level of ITIH3 is about 1.9 fold higher than the expression level of ITIH3 in a control.

As shown herein, in some embodiments, use of ITIH3 to detect gastric cancer provides a specificity and sensitivity of about 66% and 96%, respectively. In other embodiments, detection of gastric cancer is achieved with greater than about 80%, 81%, 82%, 83%, 84%, 85%, 86%, 87%, 88%, 89%, 90%, 91%, 92%, 93%, 94%, 95%, 96%, 97%, 98%, or 99% sensitivity. In yet other embodiments, the detection of gastric cancer is achieved with about 66%, 67%, 68%, 69%, 70%, 80%, 81%, 82%, 83%, 84%, 85%, 86%, 87%, 88%, 89%, 90%, 91%, 92%, 93%, 94%, or 95% specificity. In another embodiment, detection of gastric cancer is achieved with greater than about 96% sensitivity and about 66% specificity.

The methods for detecting gastric cancer is an individual can be used for a variety of purposes such as for diagnostic and/or prognostic purposes for predicting (or indicating) a clinical outcome (e.g., relapse, metastasis, survival) of a newly diagnosed gastric cancer patient or a gastric cancer patient that is undergoing or has undergone therapy. For example, ITIH3 can be used to screen asymptomatic and symptomatic subjects and to differentiate between benign and malignant diseases. In addition, ITIH3 can be used as a prognostic marker for gastric cancer.

In a particular aspect, the present invention provides for methods of monitoring an individual at risk for developing gastric cancer (e.g., an individual that does not uet have gastric cancer or has not yet een diagnosed with gastric cancer such as an individual with a personal or first-degree family history of gastric cancer; an individual that produces higher than normal levels of ITIH3). The method comprises (consists essentially of consists of) determining an ITIH3 expression level in the individual, wherein an increase in the expression level of ITIH3 in the individual compared to the control is indicative of an individual at risk for developing gastric cancer. The expression level of ITIH3 of an individual can be monitored at regular intervals (e.g., once every 6 months; once a year; once every two years) in order to determine whether the expression levels of ITIH3 in the individual change (e.g., decreases, increases) over time. An indication that the expression level of ITIH3 is increasing over time in the individual is an indication that the individual is at risk for developing, or has developed, gastric cancer.

In another aspect, the invention provides for a method of detecting recurrence of gastric cancer in an individual in need thereof (e.g., an individual that has been treated for gastric cancer and is in remission) comprising (consists essentially of; consists of) determining an ITIH3 expression level in the individual, wherein an increase in the expression level of ITIH3 in the individual compared to the control is indicative of recurrence of gastric cancer in the individual.

Also encompassed by the present invention is a method of monitoring a treatment regimen for gastric cancer in an individual in need thereof comprising (consists essentially of consists of) monitoring an expression level of ITIH3 in the individual (e.g., an individual that has been treated for gastric cancer using, for example, drugs (chemotherapeutic drug) and/or surgery). An expression level of ITIH3 in the individual that is substantially the same as or lower (decreased; less than) than the expression level of ITIH3 in a control sample is indicative of a successful treatment regimen; and an expression level of ITIH3 in the individual that is higher (increased; greater than) than the expression level of ITIH3 in the control is indicative of an unsuccessful treatment regimen.

In another aspect, the present invention provides a method of differentiating between a benign gastric disease and a malignant gastric disease in an individual in need thereof (e.g., a symptomatic individual, an asymptomatic individual). The method comprises (consists essentially of; consists of) determining an ITIH3 expression level in the individual, wherein an increase in the expression level of ITIH3 in the individual compared to the control is indicative of a malignant gastric disease in the individual. Conversely, an expression level that is similar to, or decreased, in the individual compared to the control level is indicative of a benign gastric disease in the individual.

In yet another aspect, the present invention provides a method of screening an asymptomatic individual for gastric cancer comprising determining an ITIH3 expression level in the individual, wherein an increase in the expression level of ITIH3 in the individual compared to the control is indicative of gastric cancer in the individual.

The invention also provides an article of manufacture, also referred to herein as a kit, for use in diagnosis of gastric cancer. For example, the kit can include a labeled compound or agent (e.g., an antibody, an enzyme) capable of detecting (specifically detecting) the expression level of ITIH3 in a sample; means for determining the amount in the sample; means for comparing the amount in the sample with a control (standard); and/or a suitable control. The component(s) can be packaged in a suitable container. The kit can further comprise instructions for using the kit to detect the expression level of ITIH3. In specific embodiments, the article of manufacture comprises a composition that detects ITIH3 (e.g., ITIH3 nucleic acid or portion thereof; ITIH3 polypeptide or portion thereof; ITIH3 activity; and combinations thereof). Such compositions include a probe and or primer that detects ITIH3 nucleic acid or portion thereof; an antibody that has binding specificity for ITIH3 or portion thereof; and/or reagents that detect ITIH3 activity. The article of manufacture can also include manufacturer's instructions for use and packaging material.

The methods described herein can be used alone or together with current clinical tests for better diagnosis of gastric cancer. The methods described herein have advantages in terms of sensitivity and specificity of detecting gastric cancer.

EXEMPLIFICATION

Methods and Materials
MKN45 Xenograft in Nude Mice

All animal work was done with IACUC approval and complies with the Agri-Food and Veterinary Authority of Singapore (AVA) guidelines. BALB/C-nu strain female nude mice (4-6 weeks) were purchased from Biological Resources Centre (BRC), Agency for Science, Technology and Research (A*STAR). These mice were caged and maintained using laminar air-flow rack.

Human gastric cancer cell line MKN45, a poorly differentiated adenocarcinoma was purchased from Japanese Riken Cell Bank (Tsukuba, Japan). Others cell lines including MKN28, N87-HCl, SCH, KAT03, SNU1, SNU16, IM95, NUGC3, NUGC4, SNU719, MKN74, N87, OCUM1, SNU84, HGC27, HS746T, TMK1, AZ521 and SNU620 were purchased from either American Type Culture Collection (Manassas, V A) or Japanese Riken Cell Bank (Tsukuba, Japan), whereas HFE-145 normal gastric epithelial cell was a courtesy from Dr. Hassan Ashktorab (Howard University Cancer Center, Washington D.C., USA). These cells were cultured in controlled humidified atmosphere containing 5% $CO_2$ at 37° C. using RPMI 1640 media supplemented with 10% fetal calf serum.

Trypsinised and pelleted MKN45 cells were washed and re-suspended in PBS buffer. A total of $5 \times 10^6$ cells were transplanted by subcutaneous inoculation into the left flank of 15 mice (i.e. 5 mice per group). The MKN45 mice xenografts were sacrificed once the tumor size reached approximately: a) 1-2 mm for low tumor burden group, b) 7.5 mm for mid-tumor burden group and c) 15 mm for high tumor burden group. Five control mice were injected with Phosphate Buffered Saline (PBS) buffer and were sacrificed at the middle time point of the study, about 4 weeks after the injection. Blood from each group was collected into $K_2EDTA$ Microtainer tube (BD, USA) via cardiac puncture using 23G butterfly needle. Following centrifugation at 1,100×g at 4° C. for 10 min to separate plasma from the red blood cells, protein inhibitors were added to the plasma sample. Separate pools of individual mice were stored at −80° C.

Sample Preparation, ITRAQ™ Labeling and LC-MS/MS Analysis

The same volume (50 μL) of plasma samples from each mouse were pooled according to the groups they are in (i.e. control, low, mid and high tumor burden groups). The pooled samples were depleted using Removal System (MARS Ms-3) affinity column (Agilent Technologies, CA, USA). Depleted plasma samples were then concentrated and washed 3 times with 50 mM TEAB buffer pH 8 on 5 kDa cut-off centrifugal filter units (Millipore), prior to BCA assay.

Protein samples were then reduced, alkylated, digested and labeled with iTRAQ™ reagents according to the recommended protocol (Applied Biosystems, Framingham, Mass., USA). The samples were labeled as follow: 114—control, 115—low tumor burden, 116—mid tumor burden and 117—high tumor burden. Triplicate replicate set of iTRAQ™ experiments were carried out to increase the reliability of the results. Dried labeled peptide mixture was fractionated using a PolySULFOETHYL™ A Column (PolyLC, Columbia, Md., USA) 5 μm of 200 mm length×4.6 mm ID, 200 Å pore size, on an AKTA™ Purifier FPLC unit (GE Healthcare, UK) using a 60 min gradient. A total of 30 fractions were pooled and cleaned-up using a C18 Discovery® DSC-18 SPE column (100 mg capacity, Supelco, Sigma-Aldrich).

Those fractions were then analyzed using Ultimate® 3000 nano-flow HPLC (Dionex, Surrey, UK) coupled online to a quadruple time of flight mass spectrometer (QStar™ XL, Applied Biosystems). Samples were re-suspended in 0.1% formic acid and 2% acetonitrile in water (Buffer A), prior loading to a 5 cm×300 μm ID LC-Packing C18 100 Å PepMap100 trap cartridge for desalting at 20 μL/min for 5 min. Then the trap was switched online with a 15 cm×75 μm ID LC-Packing C18 100 Å PepMap100 analytical column. A 120 min or 85 min gradient was used, ramping from 5% to 100% Buffer B (0.1% formic acid in 98% acetonitrile) in 2 linear gradient steps to elute peptides. Eluent from the reverse phase nLC was directly subjected to positive ion nanoflow electrospray analysis in an information dependant acquisition mode (IDA), with a ToF MS survey scan was acquired (m/z 300-1800), with the 3 most intense multiple charged ions (counts>20) were sequentially subjected to MS/MS analysis. The time of summation of MS/MS events was set to be 2 sec in the mass range of m/z 100-1600.

Protein identification and quantification for iTRAQ™ samples were carried out using ProteinPilot™ software (version 2.0; Applied Biosystems, MDS-Sciex). The search was performed against IPI mouse database (version 3.56, date of release: March 2009, 56073 sequences). The search was performed using Paragon Algorithm™, which is discussed in detail in Shilov, L. V. et al., *Mol Cell Proteomics* 2007, 6, (9), 1638-55. Only those proteins identified with at least 95% confidence were taken into account. All results were then exported into Excel for manual data interpretation.

Clinical Plasma Samples

Since January 2006, patients with newly diagnosed gastric cancer at the National University Hospital and Tan Tock Seng Hospital, Singapore, have been prospectively enrolled with informed consent in a research study (Gastric Cancer Biomarker Discovery II, GASCAD II) and blood samples obtained together with clinical and pathologic annotation. Blood collection was obtained before surgery or chemotherapy. Staging information was determined histopathologically and in combination with all clinical information. There was no evidence of other malignancies. American Joint Committee on Cancer (AJCC) ($6^{th}$ edition) on gastric cancer staging system and Lauren's classification of gastric cancer were used. Non-cancer controls were obtained from a clinical study in which subjects had undergone screening with upper gastrointestinal endoscopy which determined they were free of gastric cancer. The same blood collection protocols were used in all patients. The study was approved by the respective institutional review boards and all patients gave written informed consent.

Western Blotting and Immunohistochemistry

To validate iTRAQ™ result, the same pooled mouse plasma samples used for iTRAQ™ analysis were subjected to immunoblotting against ITIH3 and LIFR (Santa Cruz), as previously described (Lim, Y. P. et al., *J Biol Chem* 1999, 274, (27), 19025-34; Lim, Y. P. et al., *Mol Cancer Ther* 2003, 2, (12), 1369-77). Triplicates blots were carried out for each sample to ensure robustness of data generated. For human plasma validation, a total of 167 samples, comprising 83 normal and 84 gastric cancer samples were screened for ITIH3 expression. Plasma protein from each sample was loaded into 1D-SDS PAGE. Gel strips spanning the desired molecular weight range were cut out from various 1D gels, laying onto the same PVDF membrane and Western blotted using ITIH3 and secondary antibodies at 1:1000 and 1:15000, respectively. The densitometry of these bands was analyzed and estimated using linage Scanner and ImageQuant™ TL software v2003.03 (General Electric Healthcare).

For immunohistochemistry, matched malignant and adjacent normal gastric tissues and the histopathology reported were requested from the Tissue Repositories of National Cancer Centre of Singapore (NCCS) and National University Hospital (NUH) following approvals from Institutional Review Board from NCCS, NUH and National University of Singapore. Immunohistochemistry was carried out as previously described (Chen, Y. et al., *Mol Cell Proteomics* 2007, 6, (12), 2072-87; Ho, J. et al., *J Proteome Res* 2009, 8, (2), 583-94), with primary antibody (ITIH3) at 1:500 dilutions. All interpretations of H&E sections and analysis/scoring of IHC data were all done by the same certified pathologist to maintain consistency.

Statistical Analysis

To investigate statistically differences of the protein expression level obtained via immunoblot in normal plasma compared to cancer plasma, 2-sample Student's t-test analysis was performed at 5% significance using SPSS16.0 software for Windows. All other statistical analyses including Fisher's exact test, Kruskal-Wallis test, and likelihood ratio test were also performed using the aforementioned statistical software. Receiver operating characteristics (ROC) curve was also generated to estimate the protein sensitivity and specificity using Stata 10.0 software package (Stata Corp, Texas, USA).

Results

Identification and Relative Quantification of Mouse Plasma Proteins

All experimental mice developed tumors after 5 days of inoculation. The volumes of tumors for the low-, mid- and high-tumor burden groups of mice ranged from 2.1-2.5 mm$^3$, 127.4-210.2 mm$^3$ and 726.1-1077.5 mm$^3$, respectively (FIG. 1). These various sampling time points allow closer monitoring of tumor progression via protein profiling.

To profile the protein expression levels in MKN45 mouse xenograft model, quantitative iTRAQ™ approach was employed. Triplicate iTRAQ™ replicates were carried out to ensure result reproducibility and reliability. Only common proteins identified across the iTRAQ™ triplicates were considered further. Similarly with previous studies, proteins were considered up or down-regulated when their ratio were >1.3 or <0.77, with their p-value<0.05. This cut-off is widely accepted and adapted (Chen, Y. et al., *Mol Cell Proteomics* 2007, 6, (12), 2072-87; Gan, C. S. et al., *J Proteome Res* 2007, 6, (2), 821-7; Pierce, A. et al., *Mol Cell Proteomics* 2008, 7, (5), 853-63). To add further stringency to the data analysis, only proteins identified with the same protein expression trend across the three iTRAQ™ experiments were listed in the Table. The Table shows 31 proteins whose expression levels differed between at least 1 tumor loads compared to control.

Figure 2:
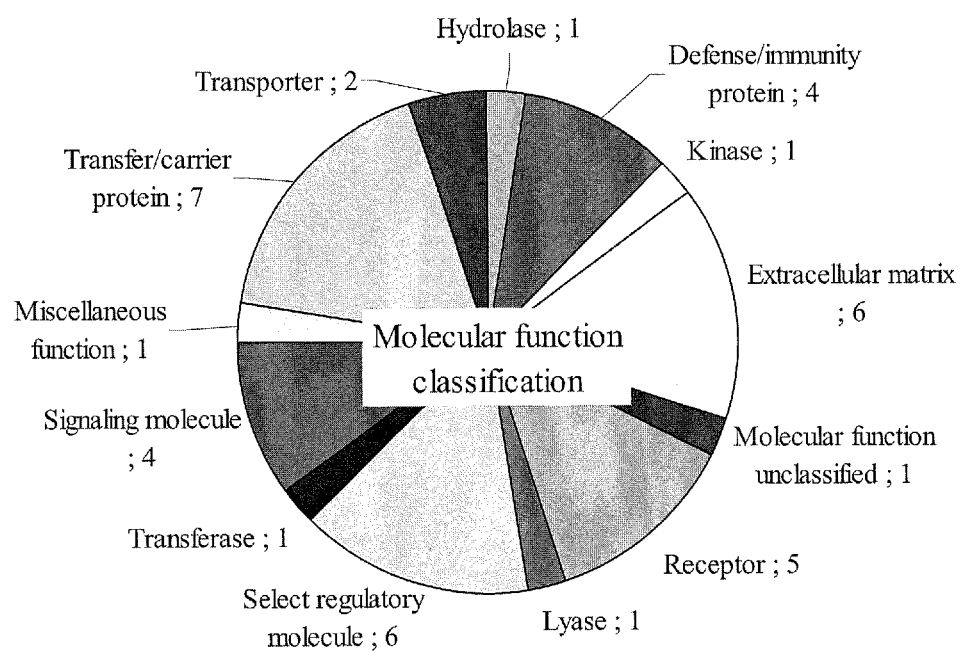
FIG. 2 shows the protein molecular function classification of the 31 common Proteins identified with similar iTRAQ™ trend across 3 iTRAQ™ replicates. The classification was performed using Panther classification systems. A total of 40 assignments were obtained and sorted into 13 molecular classifications, despite that there were only 31 proteins, as some of these proteins were assigned with more than 1 classification. The number showed in each category represented the number of protein assignment in a particular classification. The details for each classification are—Defense/immunity protein (MbI2, Saa4, Apcs, C9); Extracellular matrix (Fga, Lrgl, Lum, Fgb, Igfals, Fgg); Hydrolase (GpldI); Kinase (Egfr); Lyase (Car2); Miscellaneous function (Orm2); Molecular function unclassified (Apoc4); Receptor (Lifr, Egfr, Lrgl, Lum, Igfals); Select regulatory molecule (Itih3, Itih2, Serpina3k, Ambp, Itih1, Serpinald); Signaling molecule (Fga, Egfr, Fgb, Fgg); Transfer/carrier protein (Hbb-b2, Apoc1, Saa4, Apod, Hbb-b1, Rbp4, Hba-a2;Hba-a); Transferase (F13a1); Transporter (Apoc1, Saa4).

The molecular function classification of these 31 common proteins was achieved using the Panther Classification Thomas, P. D. et al., *Genome Res* 2003, 13, (9), 2129-41). A total of 40 protein assignments were obtained and sorted into 13 molecular classifications, since some of these proteins have multiple classifications assigned (FIG. 2). Majority of the common proteins were grouped under transport/carrier protein followed by defense/immunity protein and select regulatory molecule—typical of proteins found in the plasma.

Novel Candidates for Gastric Cancer Detection

As seen from the Table, Rbp4 was the most interesting candidate since it is highly overexpressed in all 3 groups of tumor load. However, when compared to the human gastric cancer plasma data set, this protein was found to be under-expressed in gastric cancer patients compared to cancerfree subjects. Because of the non-congruence of the data between the human and mouse plasma data set, Rbp4 was dropped from this study. Instead to add rigor to the study, we focused on 9 of the 31 candidates that had similar iTRAQ™ trend in the human gastric cancer plasma dataset.

Since the objective was to identify new and better markers than current ones, intensive literature search against Pubmed was carried out to identify proteins that were not previously associated with gastric cancer plasma detection. Two candidates proteins were finalized i.e. isoform 2 of leukemia inhibitory factor receptor (LIFR) and inter-alpha-trypsin inhibitor heavy chain H3 (ITIH3). Based on the iTRAQ™ result, LIFR protein was found to be under-expressed in both the mid and high tumor load mice, whereas ITIH3 was found to be highly expressed in high tumor load mice compared to control (the Table).

Figure 3A:
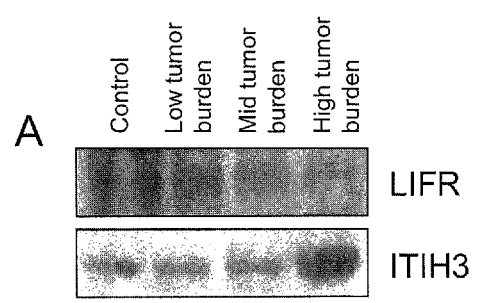
FIG. 3A shows representative immunoblots of LIFR and ITIH3 validation.
Figure 3B:
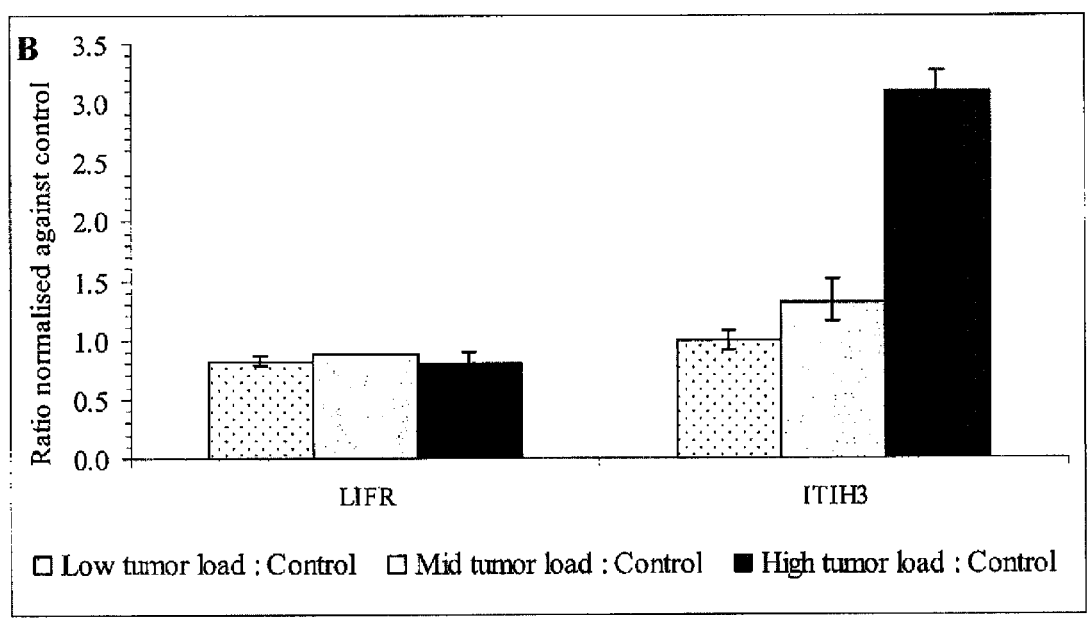
FIG. 3B shows a bar chart of the average densitometry ratio obtained from the triplicate immunoblots of both LIFR and ITIH3 proteins. The trends observed in the immunoblotting were similar to the protein expression level obtained via iTRAQ™ approach in which (i) LIFR was found to be marginally under-expressed in both mid and high tumor load and (ii) ITIH3 was highly expressed in high tumor load when compared against control.
Figure 3C:
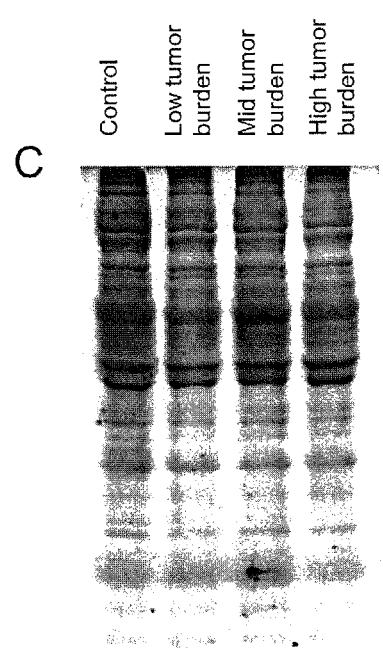
FIG. 3C shows the overall protein profile of the pooled plasma samples from control, low, mid and high tumor load mice. The gel was stained with SYPRO® Ruby to ensure equal loadings during immunoblotting analysis.

To validate the expression level of these 2 proteins indicated by iTRAQ™ analysis, the same pooled samples used for iTRAQ™ analysis were probed for both LIFR and ITIH3 expression level via immunoblotting. The results obtained via immunoblotting were found to be congruent with the expression trend revealed by the iTRAQ™ method (FIG. 3A). LIFR was found to be marginally under-expressed in mid and high tumor load mice compared to normal, with an average densitometry ratio of 0.88 and 0.80 respectively (FIG. 3B). For ITIH3, immunoblotting results showed an over-expression by 3.1-fold in high tumor load mice compared to normal. These results were obtained from triplicate immunoblots and equal loadings in these experiments were also inspected (FIG. 3C). Attaining consistent observations from two independent approaches (iTRAQ™ and immunoblotting) authenticated the findings.

ITIH3 Expression in Human Plasma

Figure 4A:
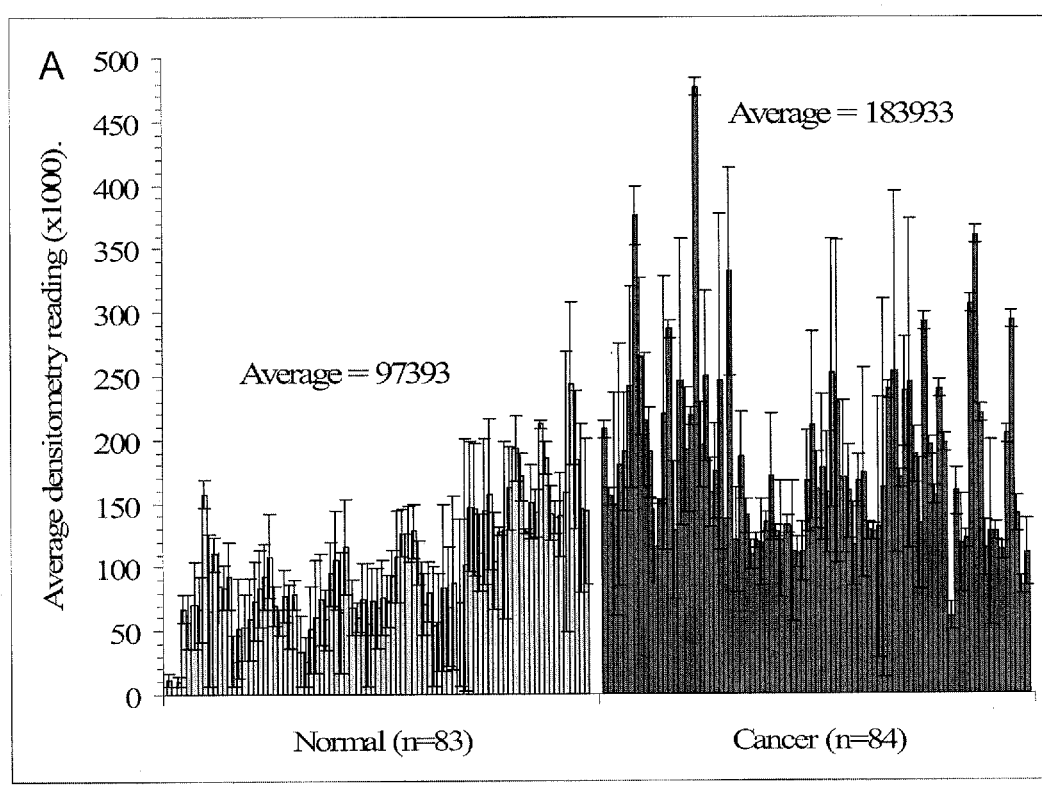
FIG. 4A shows triplicate immunoblots that were carried out for each individual and their average densitometry reading which were plotted in the bar chart according to their classification i.e. normal and gastric cancer patients. The average densitometry reading for both the overall normal subject and gastric cancer group was also calculated and shown in the chart. The average expression level of ITIH3 in gastric cancer patients was found to be 1.9-fold higher compared to normal.
Figure 4B:
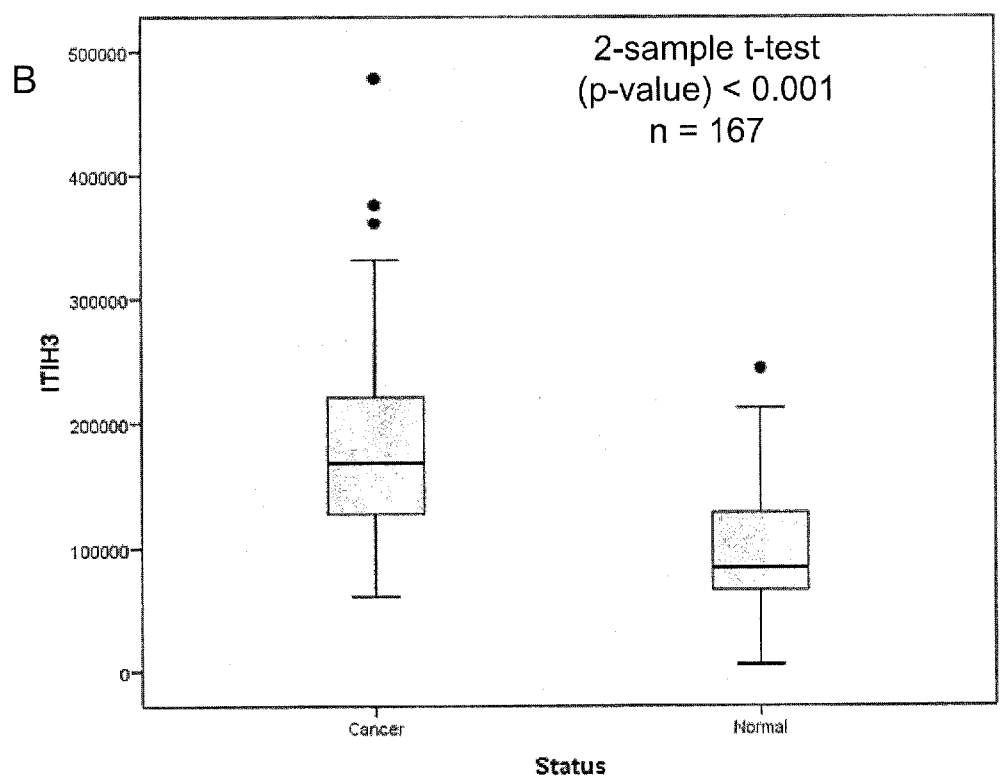
FIG. 4B shows the 2-sample t-test analysis carried out using the average densitometry for each individual samples for the two categories. Significant difference (p-value<0.001) in ITIH3 expression level was observed between normal versus cancer groups.
Figure 4C:
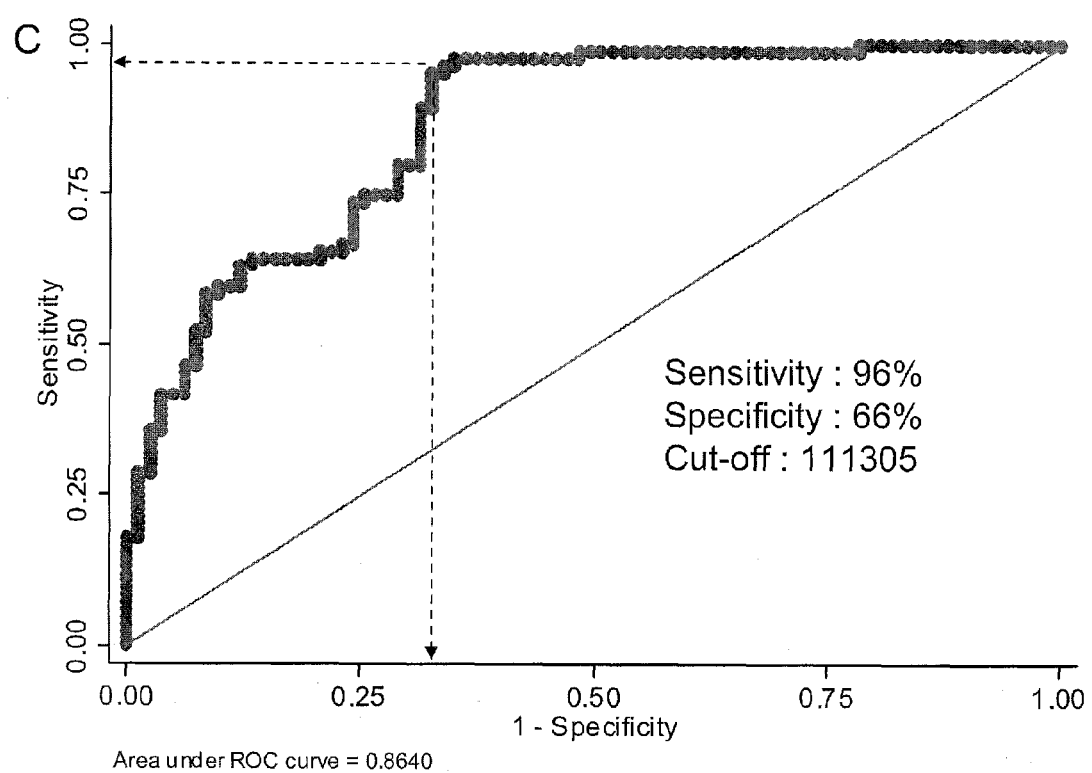
FIG. 4C shows the receiver operating characteristics (ROC) curve using ITIH3 average densitometry reading for all individual plasma samples (167) screened in the study. ITIH3 sensitivity and specificity in detecting gastric cancer were estimated to be 96% and 66% at the cutoff point of the average densitometry reading of 111305.

Since the change in expression level of ITIH3 was significantly higher in both immunoblotting and iTRAQ™ approach, ITIH3 expression level in human plasma samples was investigated to determine whether it was a viable biomarker candidate for gastric cancer detection. A total of 167 plasma samples, comprising 83 normal (cancer free) and 84 gastric cancer patients were subjected to immunoblotting with ITIH3 antibody. Triplicate blots were carried out and the average densitometry reading of ITIH3 expression for each sample was tabulated according to the samples type (normal or cancer). The average densitometry reading for each patient was plotted in a bar chart according to the samples' nature (FIG. 4A). The average densitometry of ITIH3 expression level for cancer group (183933) was found to be 1.9-fold higher compared to the normal control group (97393). A 2-sample t-test was carried out, revealing a p-value of less than 0.001 (FIG. 4B), indicating that expression level of ITIH3 can be used to discriminate the gastric cancer group from normal control. A receiver operating characteristics (ROC) curve was generated based on these results to estimate ITIH3 sensitivity and specificity in gastric cancer detection. As shown in FIG. 4C, at an average densitometry reading cut-off of 111305 units, the area under the ROC curve was estimated to be 0.864, giving ITIH3 a specificity and sensitivity of 66% and 96%, respectively at 95% confidence for gastric cancer detection.

Figure 4D:
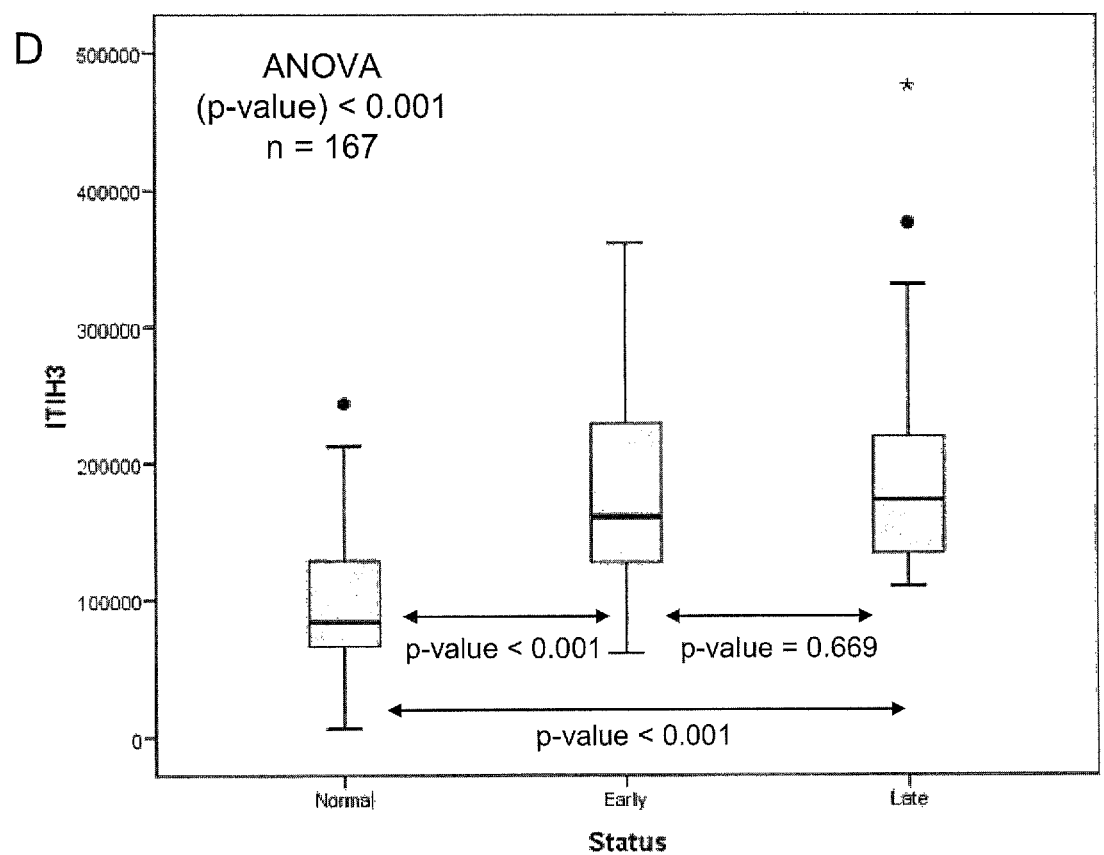
FIG. 4D is a box-plot showing the distribution of ITIH3 expression within normal, early and late stage gastric cancer Analysis of variance (ANOVA) analysis performed showed that a significant difference (p-value<0.001) in ITIH3 expression level was observed between normal versus early stage and late stage gastric cancer groups.

As early detection of gastric is an important goal, whether ITIH3 was capable of differentiating early stage gastric cancer patients from non-cancer subjects was investigated. To this end, the gastric cancer patients were segregated according to their disease stages i.e. early stage (I-II) and advanced stage (III-IV) based on American Joint Committee on Cancer (AJCC) staging system. Among the 84 gastric cancer samples screened, 36 were from early and from late stage gastric cancer. The box-plot in FIG. 4D generated from ANOVA statistical analysis revealed that the difference in ITIH3 expression level was significant (p-value<0.001) between normal subjects and early stage gastric cancer patients.

*Heliobacter pylori* (HP) infection and gastritis are frequently associated with gastric cancer. To ensure that ITIH3 was not a marker for these events, whether there was any statistically significant correlation between ITIH3 expression level and HP or gastritis status was investigated. To investigate the former, 2-sample t test statistical analyses was performed. No significant difference in the mean level of ITIH3 expression between HP-positive and HP-negative subjects were obtained (p-value=0.187). Similarly, gastritis status had no impact on ITIH3 expression, in which Fisher's extract test showed a p-value of 1.00. From a clinical and biological point of view, diffuse and intestinal types of gastric cancer have different behaviors. Thus, it was asked whether ITIH3 expression in the plasma might be different between the cancer subtypes by performing the Kruskal-Wallis test. Results showed no significant correlation (p-value=0.226) between ITIH3 expression with the various histology types. Thus, the statistical analyses indicated that plasma ITIH3 expression was independent of the HP infection, gastritis inflammation, and the histology type of gastric cancer.

To test the role of ITIH3 as a biomarker, a small-scale blinded study was performed using the cutoff value obtained from the ROC plot to predict whether the plasma sample tested was from cancer or non-cancer subject. For this purpose, 39 newly collected plasma samples (19 from normal and 20 from gastric cancer) were analyzed using the immunoblotting approach. Samples with ITIH3 average densitometry reading of less than 111 305 units were considered as normal, whereas higher than 111 305 units were considered as cancer. Using these criteria, 18 out of 20 gastric cancer plasma samples were correctly predicted, giving a sensitivity of 90%. On the other hand, among the 19 normal samples screened, only 9 of them were correctly predicted, giving ITIH3 specificity of 47%. The performance of ITIH3 in the blind test study was comparable to that revealed by the ROC curve.

ITIH3 Expression in Gastric Cancer Cells

Figure 5B:
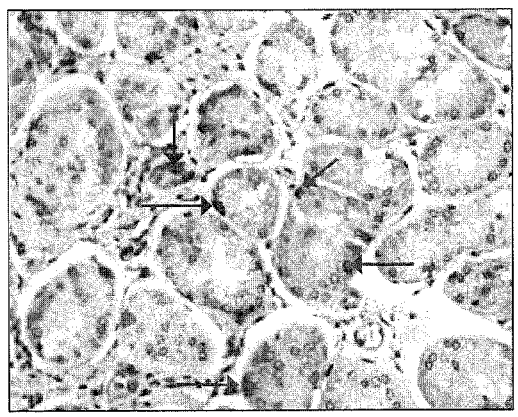
FIG. 5B is an illustration of ITIH3 expression level in normal tissue, in which ITIH3 expression was found to be randomly expressed in discrete individual cell across the tissue, as shown by the arrows in the figure.
Figure 5C:
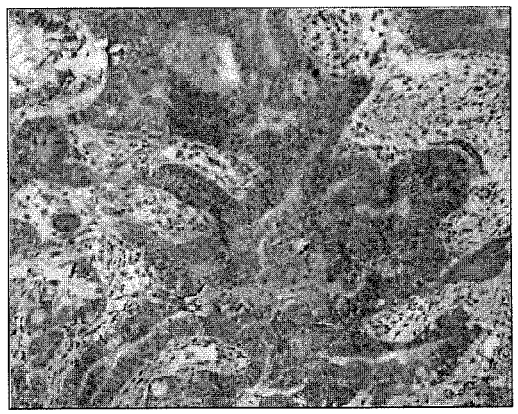
FIG. 5C shows an example of ITIH3 expression in tumor tissue, where ITIH3 expression was wide spread in many cancer cells.

Next, the expression level of ITIH3 in gastric cancer tissues was investigated. As a pilot study, 19 matched pairs of normal and gastric cancer tissues were subjected to immunohistochemistry. FIG. 5A summarized the results obtained. Forty two percent of the cases (8/19) showed no difference in ITIH3 level between tumor and normal tissue. Twenty one percent of cases (4/19) showed higher ITIH3 expression and 26% (5/19) showed lower ITIH3 expression in the tumors when compared to their matched adjacent normal tissue. In cases where normal tissues stained positive for ITIH3, only discrete individual cells expressing ITIH3 were found as shown in FIG. 5B. This reflects that only specific cells in the crypts expressed ITIH3. In contrast, ITIH3 expression in cancer cells of tumor sections was usually very wide spread (FIG. 5C). Likelihood ratio test carried out showed no significant difference (p-value=0.236) between ITIH3 expression and various histological types of gastric cancer.

Figure 5D:
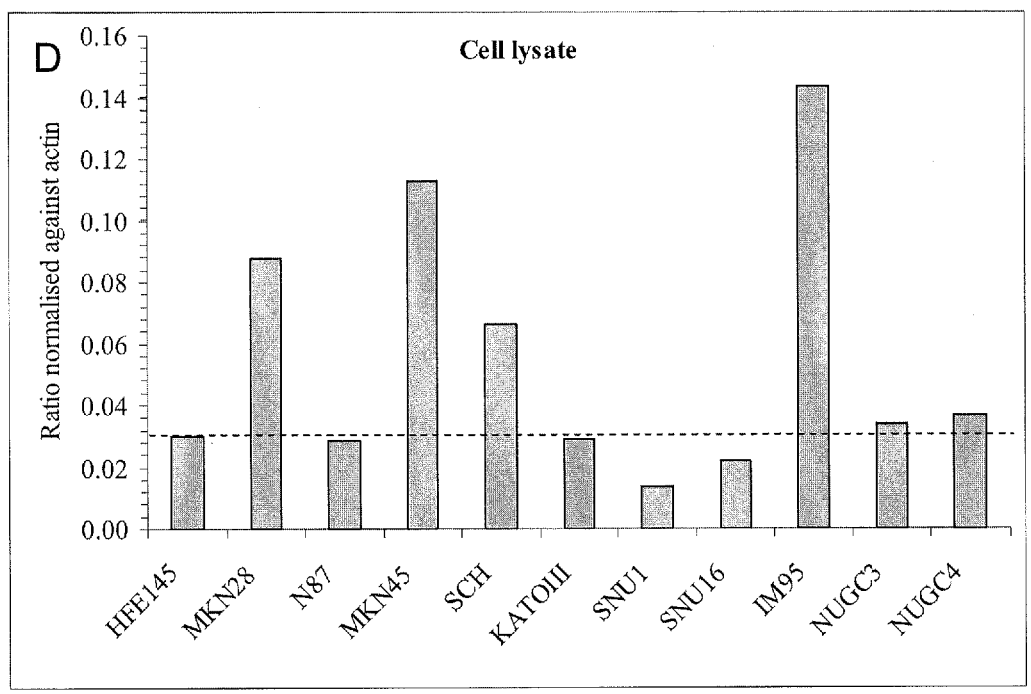
FIG. 5D shows ITIH3 expression level in a panel of gastric cancer cell lines, compared to the normal gastric cell line, HFE145. The dotted line in the figures highlighted ITIH3 expression level in normal gastric cell line HFE145.

The expression of ITIH3 in a panel of 10 gastric cancer cell lines was also examined. As shown in FIG. 5D, only 1 of the gastric cell lines (MKN45) showed overexpression of ITIH3 by 1.5-fold. Another one (SNU719) showed a 1.3-fold overexpression while 4 others (MKN74, SNU1, NUGC3 and HGC27) showed only 1.2-fold. The IHC and cell line data are largely consistent, and collectively, they implied that the up-regulation of ITIH3 in the plasma is unlikely to be the result of up-regulation of ITIH3 in cancer cells. Instead, these data supported the notion that the increase in ITIH3 plasma level could be the result of host response to the tumor. It further indicates that plasma rather than tissue is a better substrate for profiling ITIH3 during diagnostic examination.

Discussion

Xenograft model facilitates target candidate identification for validation in human clinical samples, as exemplified by the discovery of the higher expression of ITIH3 protein in the plasma of gastric tumor-bearing mice and gastric cancer patients compared to normal condition. The data provided herein showed elevated ITIH3 expression in the plasma of gastric cancer patients. Interestingly, ITIH3 has also been recently reported to be up-regulated in the sera of lung cancer of c-myc transgenic mice (Chattelji, B.; Borlak, J., *Proteomics* 2009, 9, (4)) and lung cancer patients (Heo, S. H. et al. *Proteomics* 2007, 7, (23), 4292-302).

ITIH3 is one of the five heavy chains (ITIH1, ITIH2, ITIH3, ITIH4 and ITIH5) belonging to the family of inter-alpha-trypsin inhibitor, comprising a family of protease inhibitors that are found in extracellular matrix of various organs including blood circulation. One of the well-known functions of these heavy chains is the ability to link covalently to hyaluronic acid (HA), a major component of extracellular matrix (Huang, L. et al., *J Biol Chem* 1993, 268). A study proposed that ITIH acts as an important factor to stabilize the extracellular matrix (Zhuo, L. et al., *J Biol Chem* 2004, 279, (37), 38079-82). There are evidences showing ITIH's antagonistic relationship with tumor invasion and metastasis (Kobayashi, H. et al., *J Biol Chem* 1995, 270, (14), 8361-6; Kobayashi, H. et al., *Int J Cancer* 1995, 63, (3), 455-62). Studies so far have ascribed a tumor suppressor role for ITIH, which largely exerts a negative effect on cancer progression. For example, Paris et. al. reported that ITIHI and ITIH3 expression significantly reduced the number of lung metastases in mouse xenograft and increased cell attachment in vitro (Paris, S.; Sesboue, R. et al., *Int J Cancer* 2002, 97, (5), 615-20). Another study demonstrated that down regulation of ITIH5 expression is a prognostic marker for tumor invasion and metastasis (Veeck, J. et al., *Pathologe* 2008, 29 Suppl2, 338-46; Veeck, J. et al. *Oncogene* 2008, 27, (6), 865-76). The reported loss of ITIH genes including ITIH3 expression level in the tissues of multiple solid cancers including that of the breast, stomach, lung, ovary and colon (Hamm, A. et al., *BMC Cancer* 2008, 8) seem to contradict the observed up-regulation of ITIH3 in the plasma of lung cancer (Chattelji, B.; Borlak, J., *Proteomics* 2009, 9, (4); Heo, S. H. et al. *Proteomics* 2007, 7, (23), 4292-302) and, as described herein, gastric cancer subjects. Several reasons seem conceivable for this apparent discrepancy. First, the down-regulation of ITIH3 reported was based on mRNA profiling, which may not necessarily correlate with protein levels. Second, the expression profiling was performed on tissues and not in body fluids like blood. It is likely that ITIH3 has different effects in the intracellular and extracellular compartments. Consequently, its expression in these compartments might be regulated differently. Third, the ITIH3 that was present at higher levels in the plasma of gastric cancer patients did not derive from tumor/cancer cells but was instead a consequence of host response to the tumor. The detectability of ITIH3 in early stage cancer, the IHC and in vitro cell line data all supported this notion.

Currently there is no sensitive marker used for gastric cancer detection. Conventional markers including CEA, CA19-9 and CA72-4 are not effective in detecting gastric cancer. The sensitivity of these markers in gastric cancer detection ranged from 16%-63% as summarized in a review (Ebert, M. P.; Rocken, C., *Eur J Gastroenterol Hepatol* 2006, 18, (8), 847-53). Studies had also evaluated M2-pyruvate kinase (M2-PK), a tumor-associated metabolic marker for gastric cancer detection, giving the range of sensitivity and specificity of 57%-67% and 89%-95% respectively (Hardt, P. D. et al., *Anticancer Res* 2000, 20, (6D), 4965-8; Cerwenka, H. et al., *Anticancer Res* 1999, 19, (1B), 849-51). Study on gastric cancer detection using serum pepsinogen measurement had reported a sensitivity of 77% with a specificity of 73% (Dinis-Ribeiro, M. et al., *J Med Screen* 2004, 11, (3), 141-7). A mass screening in Japan also revealed large proportion of early stage gastric cancer were detected, i.e. 80% of all detected cancers, using serum pepsinogen screening (Miki, K. et al., *Dig Endosc* 2009, 21, (2), 78-81). Biomarkers for early stage gastric cancer detection remain very limited. Based on the results provided herein, the high sensitivity of ITIH3 from 90-96% and specificity of 47-66% compared to other markers shows a significant role for ITIH3 in gastric cancer detection. In a particular embodiment, ITIH3 can be used to detect early stage gastric cancer.

In conclusion, higher level of ITIH3 was detected in the plasma of gastric cancer patients compared to non-cancer subject. The data provided herein demonstrates the role of ITIH3 as a biomarker for gastric cancer screening.

TABLE

The list of 31 differentialy expressed proteins identified in the three independent iTRAQ replicates. Only those proteins found to have similar protein regulation across the 3 iTRAQ replicates were considered significant. The expression ratio of the proteins identified in low, mid and high tumor load mice normalized against the control mice. A cut-off point of ±30% variation and p-value < 0.05 were taken into consideration. Ratio in italic indicates those differentially expressed proteins identified when compared to control. Other details information such as p-valu and error factor are tabulated in Supplementary Table 2.

| Gene Symbol | Protein Name | iTRAQ ratio of Low Tumor Load:Control | | | iTRAQ ratio of Mid Tumor Load:Control | | | iTRAQ ratio of High Tumor Load:Control | | |
|---|---|---|---|---|---|---|---|---|---|---|
| | | iTRAQ Replicate 1 | iTRAQ Replicate 2 | iTRAQ Replicate 3 | iTRAQ Replicate 1 | iTRAQ Replicate 2 | iTRAQ Replicate 3 | iTRAQ Replicate 1 | iTRAQ Replicate 2 | iTRAQ Replicate 3 |
| Rbp4 | Retinol-binding protein 4 | 2.40 | 2.78 | 2.59 | 3.75 | 4.66 | 4.11 | 3.09 | 3.71 | 3.67 |
| Apcs | Serum amyloid P-component | 0.68 | 0.60 | 0.59 | 0.87 | 0.84 | 0.86 | 1.26 | 1.11 | 1.20 |
| Serpina 1 d | Alph-1-antitrypsin 1-4 | 0.79 | 0.69 | 0.75 | 0.67 | 0.64 | 0.65 | 0.84 | 0.69 | 0.74 |
| Fgg | Putative uncharacterized protein | 0.83 | 0.75 | 0.74 | 0.66 | 0.56 | 0.61 | 1.36 | 1.20 | 1.18 |
| Saa4 | Serum amyloid A-4 protein | 0.91 | 0.83 | 0.89 | 0.74 | 0.68 | 0.73 | 0.93 | 0.84 | 0.93 |
| F13a1 | Coagulation factor XIII A chain | 0.98 | 0.94 | 0.88 | 0.64 | 0.67 | 0.59 | 1.17 | 1.16 | 1.13 |
| Fgb | Fibrinogen beta chain | 0.76 | 0.79 | 0.83 | 0.58 | 0.57 | 0.65 | 1.16 | 1.16 | 1.28 |
| Fga | Fibrinogen, alpha polypeptide isoform 1 | 0.8 | 0.73 | 0.78 | 0.6 | 0.54 | 0.64 | 1.29 | 1.14 | 1.27 |
| Serpina3K | Serine protease inhibitor A3K | 1.06 | 0.95 | 1.03 | 0.54 | 0.41 | 0.63 | 0.81 | 0.7 | 0.78 |
| Egfr | Epidermal growth factor receptor | 1.12 | 1.24 | 1.08 | 0.61 | 0.68 | 0.55 | 0.74 | 0.78 | 0.63 |
| Car2 | Carbonic anhydrase 2 | 1.13 | 1.02 | 1.07 | 1.48 | 1.46 | 1.61 | 1.03 | 0.87 | 1.09 |
| Hba-a2; Hba-a1 | Hemoglobin subunit alpha | 0.90 | 0.92 | 1.01 | 1.33 | 1.56 | 1.45 | 0.82 | 0.69 | 0.84 |
| Hba-a2; Hba-a1 | Hemoglobin alpha, adult chain 2 | 0.86 | 0.78 | 0.87 | 1.35 | 1.66 | 1.35 | 0.69 | 0.65 | 0.87 |
| Hbb-b1 | Hemoglobin subunit beta-1 | 0.93 | 1.42 | 0.90 | 1.50 | 2.39 | 1.46 | 0.68 | 0.96 | 0.65 |
| Hbb-b2 | Hemoglobin subunit beta-2 | 0.99 | 1.00 | 0.99 | 1.59 | 1.49 | 1.49 | 0.68 | 0.70 | 0.64 |
| LIFR | Isoform 2 of Leukemia inhibitory factor receptor | 1.01 | 0.99 | 0.95 | 0.58 | 0.54 | 0.53 | 0.37 | 0.33 | 0.34 |
| C9 | Complement component 9 | 0.96 | 0.95 | 0.86 | 0.58 | 0.53 | 0.57 | 0.61 | 0.55 | 0.57 |
| Lum | Lumican | 1.01 | 0.95 | 1.03 | 0.96 | 0.82 | 0.90 | 0.74 | 0.67 | 0.68 |
| Mb; 2 | Mannose-binding protein C | 0.93 | 0.95 | 0.93 | 0.88 | 0.91 | 0.87 | 0.66 | 0.67 | 0.64 |
| Apoc4 | Apolipoportein C-IV | 1.09 | 1.08 | 0.98 | 1.04 | 1.08 | 1.03 | 0.76 | 0.68 | 0.73 |
| Gpld1 | Glycosylphosphatidylinositol specific phospholipase D1 | 1.10 | 1.09 | 1.12 | 1.08 | 1.06 | 1.12 | 0.69 | 0.54 | 0.57 |
| Apoc1 | Apolipoprotein C-1 | 0.86 | 0.84 | 0.78 | 0.83 | 0.75 | 0.86 | 0.70 | 0.66 | 0.74 |
| Igfals | Insulin-like growth factor-binding protein complex acid labile chain | 1.23 | 1.01 | 1.24 | 0.91 | 0.75 | 0.89 | 0.76 | 0.59 | 0.69 |
| 2610016E04Rik | Hypothetical protein LOC100039008 | 1.50 | 5.66 | 0.73 | 0.49 | 0.87 | 0.34 | 0.21 | 0.39 | 0.17 |
| Orm2 | Alpha-1-acid glycoprotein 2 | 0.92 | 0.78 | 0.76 | 0.70 | 0.64 | 0.58 | 3.96 | 3.53 | 3.50 |
| Ambp | Protein AMBP | 0.80 | 1.82 | 0.87 | 1.37 | 2.54 | 0.75 | 2.85 | 4.69 | 1.72 |
| Apod | Apolipoprotein D | 0.88 | 0.86 | 0.83 | 1.08 | 1.08 | 1.11 | 1.45 | 1.52 | 1.72 |
| Lrg1 | Leucine rich alpha-2 glycoprotein 1 | 0.97 | 1.03 | 0.83 | 0.88 | 1.12 | 0.94 | 1.63 | 2.04 | 1.82 |
| Itih1 | Itih 1 protein | 1.14 | 1.09 | 1.07 | 1.15 | 1.20 | 1.13 | 1.65 | 1.65 | 1.82 |
| Itih3 | Inter-alpha-trypsin inhibitor heavy chain H3 | 0.93 | 0.88 | 0.90 | 1.34 | 1.05 | 1.05 | 3.26 | 2.80 | 2.66 |
| Itih2 | Inter-alpha-trypsin inhibitor heavy chain H2 | 1.05 | 0.98 | 1.18 | 1.21 | 1.11 | 1.31 | 1.71 | 1.55 | 1.85 |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method comprising
   a) contacting a sample obtained from an individual with an antibody or antigen binding fragment thereof having binding specificity for all or a portion of inter-alpha-trypsin inhibitor heavy chainh3 (ITIH3) protein, wherein said individual is selected from the group consisting of an individual known to have gastric cancer, and an individual in remission from gastric cancer; and wherein said sample is a sample of body fluid; and
   b) measuring any immunospecific binding that occurs between the antibody or antigen binding fragment thereof and the ITIH3 protein, and
   c) detecting an increase in the level of the ITIH3 protein in the sample relative to a control sample.

2. The method of claim 1 wherein the antibody is a polyclonal antibody or a monoclonal antibody.

3. The method of claim 1 wherein the individual is a human.

4. The method of claim 1 wherein any immunospecific binding that occurs between the antibody or antigen binding fragment thereof and the ITIH3 protein is measured using Western blotting.

5. The method of claim 1, wherein said sample is a plasma sample.

6. The method of claim 1, wherein the sample is a whole blood sample, a serum sample, or a plasma sample.

* * * * *